(12) United States Patent
Hunt et al.

(10) Patent No.: US 9,063,387 B1
(45) Date of Patent: Jun. 23, 2015

(54) SYSTEMS AND METHODS FOR APPLYING DIRECTED ENERGY TO AN OBJECT

(75) Inventors: Jeffrey H. Hunt, Thousand Oaks, CA (US); Nicholas Koumvakalis, Thousand Oaks, CA (US)

(73) Assignee: The Boeing Company, Chicago, IL (US)

( * ) Notice: Subject to any disclaimer, the term of this patent is extended or adjusted under 35 U.S.C. 154(b) by 247 days.

(21) Appl. No.: 13/614,441

(22) Filed: Sep. 13, 2012

(51) Int. Cl.
*G02F 1/39* (2006.01)
*G02F 1/35* (2006.01)
*G02F 1/37* (2006.01)

(52) U.S. Cl.
CPC ...................................... *G02F 1/353* (2013.01)

(58) Field of Classification Search
CPC .............. F21Y 2113/00; G02F 1/353–1/3538; G02F 2001/354–2001/3542; G02F 2/00–2/02; H05B 35/00; A61N 5/062; A61N 2005/0642; A61N 2005/0636; A61N 5/0624; A61N 5/0601; A61N 5/0603; A61N 5/00–5/045; A61N 5/0625; H01S 5/4087; H01S 5/4012
USPC ....................... 362/230–231, 234; 342/13–20
See application file for complete search history.

(56) References Cited

U.S. PATENT DOCUMENTS

| 4,932,775 A * | 6/1990 | Wissman et al. ............. 356/5.09 |
| 7,239,262 B2 * | 7/2007 | Osepchuk ........................ 342/22 |
| 2009/0088625 A1 * | 4/2009 | Oosting et al. ................ 600/411 |

OTHER PUBLICATIONS

U.S. Appl. No. 13/477,546, filed May 22, 2012.

* cited by examiner

*Primary Examiner* — Karabi Guharay
*Assistant Examiner* — Nathaniel Lee
(74) *Attorney, Agent, or Firm* — Armstrong Teasdale LLP

(57) ABSTRACT

Systems and methods are provided for applying directed energy to an object. The system includes a first transmitter comprising a light source configured to emit a first light beam at a first frequency towards a focal point and a second transmitter comprising a light source configured to emit a second light beam at a second frequency towards the focal point. The first and second light beams cause a third light beam to be generated that has a third frequency that is coincident with at least one resonant frequency of the object.

19 Claims, 4 Drawing Sheets

SYSTEMS AND METHODS FOR APPLYING DIRECTED ENERGY TO AN OBJECT

BACKGROUND

The field of the disclosure relates generally to light-based directed energy systems, and more specifically, to methods and systems for applying directed energy to an object.

At least some known directed energy systems use light beams to apply directed energy to an object and/or to alter a physical characteristic of the object. One method used to alter a physical characteristic of an object involves operating a directed energy system to interact with a resonant frequency of the object. For example, known directed energy sources include high-powered lasers, such as a chemical oxygen iodine laser (COIL), a hydrogen fluoride (HF) laser, and/or a deuterium fluoride (DF) laser. Such directed energy sources are single frequency directed energy sources that typically emit wavelengths in the infrared region.

However, the use of known single frequency directed energy sources is limited because the sources that generate high power are not usually naturally coincident with resonant frequencies that cause high levels of conditional change of the object. As such, known directed energy systems may be inefficient and/or ineffective at altering a physical characteristic of an object.

BRIEF DESCRIPTION

In one aspect, a system is provided for applying directed energy to an object. The system includes a first transmitter comprising a light source configured to emit a first light beam at a first frequency towards a focal point and a second transmitter comprising a light source configured to emit a second light beam at a second frequency towards the focal point. The first and second light beams cause a third light beam to be generated that has a third frequency that is coincident with at least one resonant frequency of the object.

In another aspect, a method of applying directed energy to an object is provided. The method includes emitting a first light beam at a first frequency towards a focal point, and emitting a second light beam at a second frequency towards the focal point. The method also includes mixing the first and second light beams to cause a third light beam to be generated that has a third frequency that is coincident with at least one resonant frequency of the object and applying the third light beam to a surface of the object.

The features, functions, and advantages that have been described herein can be achieved independently in various embodiments or may be combined in yet other embodiments, further details of which can be seen with reference to the following description and drawings.

DETAILED DESCRIPTION

Figure 1:
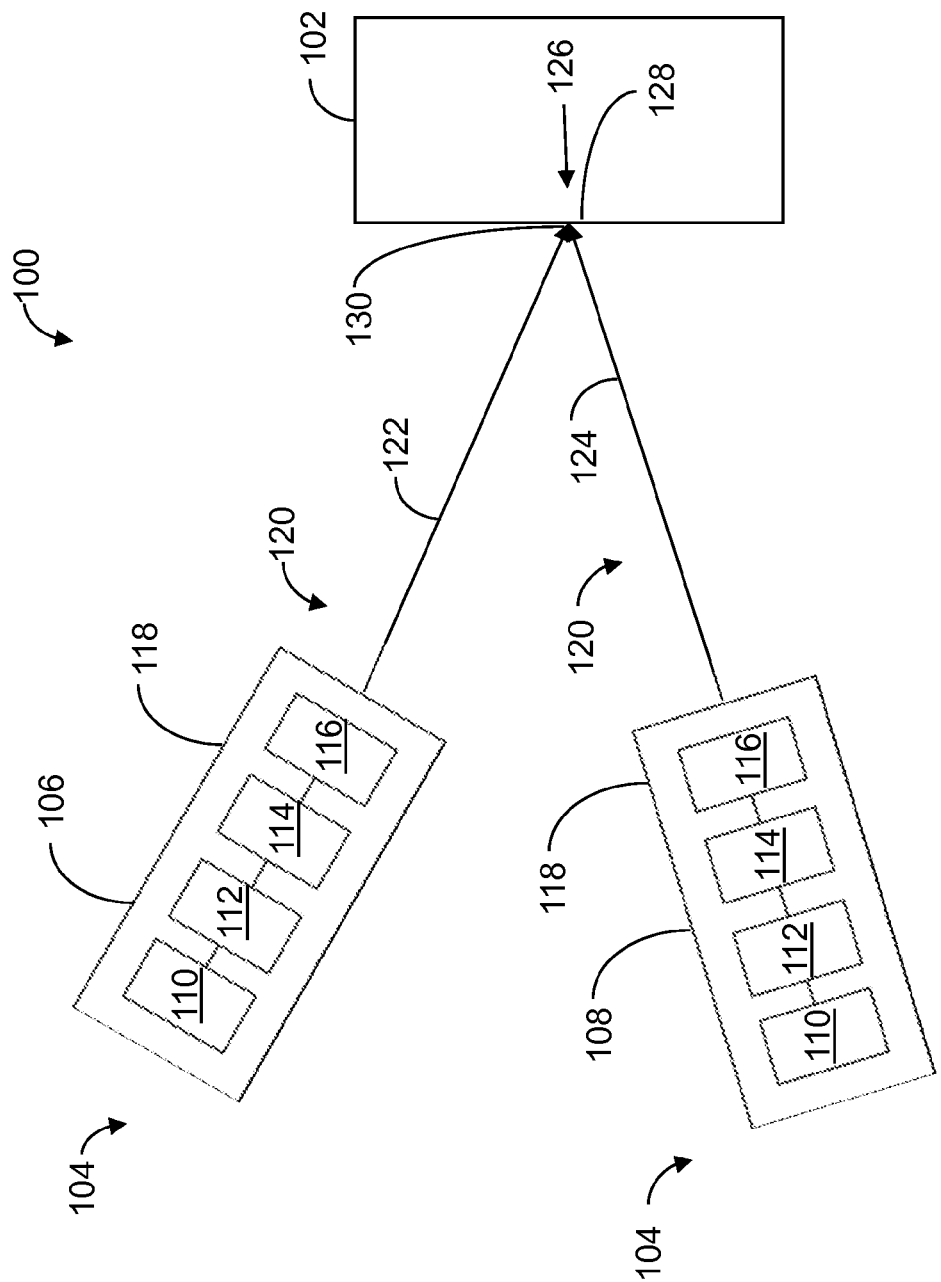
FIG. 1 illustrates an exemplary directed energy system that may be used to apply directed energy on an object and/or that may be used to change a physical characteristic of the object.

FIG. 1 illustrates an exemplary directed energy system 100 that may be used to apply directed energy on an object 102, and/or that may be used to alter a physical characteristic of object 102. In the exemplary embodiment, directed energy system 100 includes at least one transmitter 104. More specifically, in the exemplary embodiment, directed energy system 100 includes a first transmitter 106 and a second transmitter 108. Alternatively, directed energy system 100 may include any number of transmitters 104 that enables directed energy system 100 to function as described herein. Object 102 may be, but is not limited to only being, a vehicle, a building, a person, or any other object that may be least partially interact with light.

Unless otherwise specified, transmitters 104 are substantially identical, and each includes a light source 110, an output intensity control module 112, an output frequency control module 114, and an output polarization control module 116 that are each positioned within a housing 118. Light source 110 generates a light beam 120 that is emitted from transmitter 104. In the exemplary embodiment, light source 110 is a laser. Alternatively, light source 110 may be any other source that enables transmitter 104 to generate a light beam 120 as described herein.

Output intensity control module 112 is coupled to light source 110. Output intensity control module 112 receives light beam 120 from light source 110 and selectively controls and/or adjusts an intensity of light beam 120. In the exemplary embodiment, output intensity control module 112 includes a feedback system that controls and/or adjusts the intensity of light beam 120 and outputs light beam 120 at a predetermined intensity. Alternatively, output intensity control module 112 may include any other device that enables transmitter 104 to control the intensity of light beam 120 as described herein.

Output frequency control module 114 is coupled to output intensity control module 112. Output frequency control module 114 receives light beam 120 from output intensity control module 112 and controls and/or adjusts a frequency of light beam 120. In the exemplary embodiment, output frequency control module 114 includes an etalon, a passive grating, and/or an optical filter. Alternatively, output frequency control module 114 may include any other device that enables transmitter 104 to control and/or adjust the frequency of light beam 120 as described herein.

Output polarization control module 116 is coupled to output frequency control module 114 and receives light beam 120 emitted from output frequency control module 114 and controls and/or adjusts a polarization of light beam 120. In the exemplary embodiment, output polarization control module 116 includes a polarizer (not shown) and/or a wave plate (not shown). Alternatively, output polarization control module 116 may include any other device that enables transmitter 104 to control and/or adjust the polarization of light beam 120 as described herein.

In the exemplary embodiment, first transmitter 106 and second transmitter 108 emit light beams 122 at the same or at different frequencies. More specifically, in the exemplary embodiment, first transmitter 106 emits a first light beam 122 at a first frequency, and second transmitter 108 emits a second light beam 124 at a second frequency. Each light beam 122 and 124 is directed towards the same location or focal point 126. In the exemplary embodiment, focal point is on a surface 128 of object 102 such that first light beam 122 and second light beam 124 at least partially interact on surface 128.

First light beam 122 and/or second light beam 124 interact with each other at surface 128 such that material excitations are generated on surface 128. The interaction with respect to first light beam 122 and/or second light beam 124 on surface 128 generates an effective energy transfer that facilitates a more expedient change in the physical state of object 102. In some embodiments, first and second light beams 122 and 124 interact with a resonant frequency of object 102 to generate sufficient material excitations to physically destroy object 102.

As used herein, the interaction between first light beam 122, second light beam 124, and surface 128 of object 102 causes a third light beam 130 to be generated with a third frequency that is different from the frequency of the light beams received at the surface.

In the exemplary embodiment, the interaction of light beams 122 and 124 non-linear response of surface 128 causes a third light beam 130 to be generated at focal point 126. Beam 130 has a second harmonic frequency relative to first light beam 122 and of second light beam 124 that is approximately two times the frequency of first light beam 122 and/or second light beam 124. Moreover, third light beam 130 has a second order combination (i.e., a second order effect) as compared to first light beam 122 and second light beam 124. The second order effect may cause third light beam 130 to have a frequency that is approximately equal to a sum of the frequencies of first light beam 122 and second light beam 124, or a frequency that is approximately equal to a difference between the frequencies of first light beam 122 and second light beam 124. Alternatively or additionally, the frequency of third light beam 130 may be generated at any other non-linear combination relative to first light beam 122 and/or second light beam 124.

Figure 2:
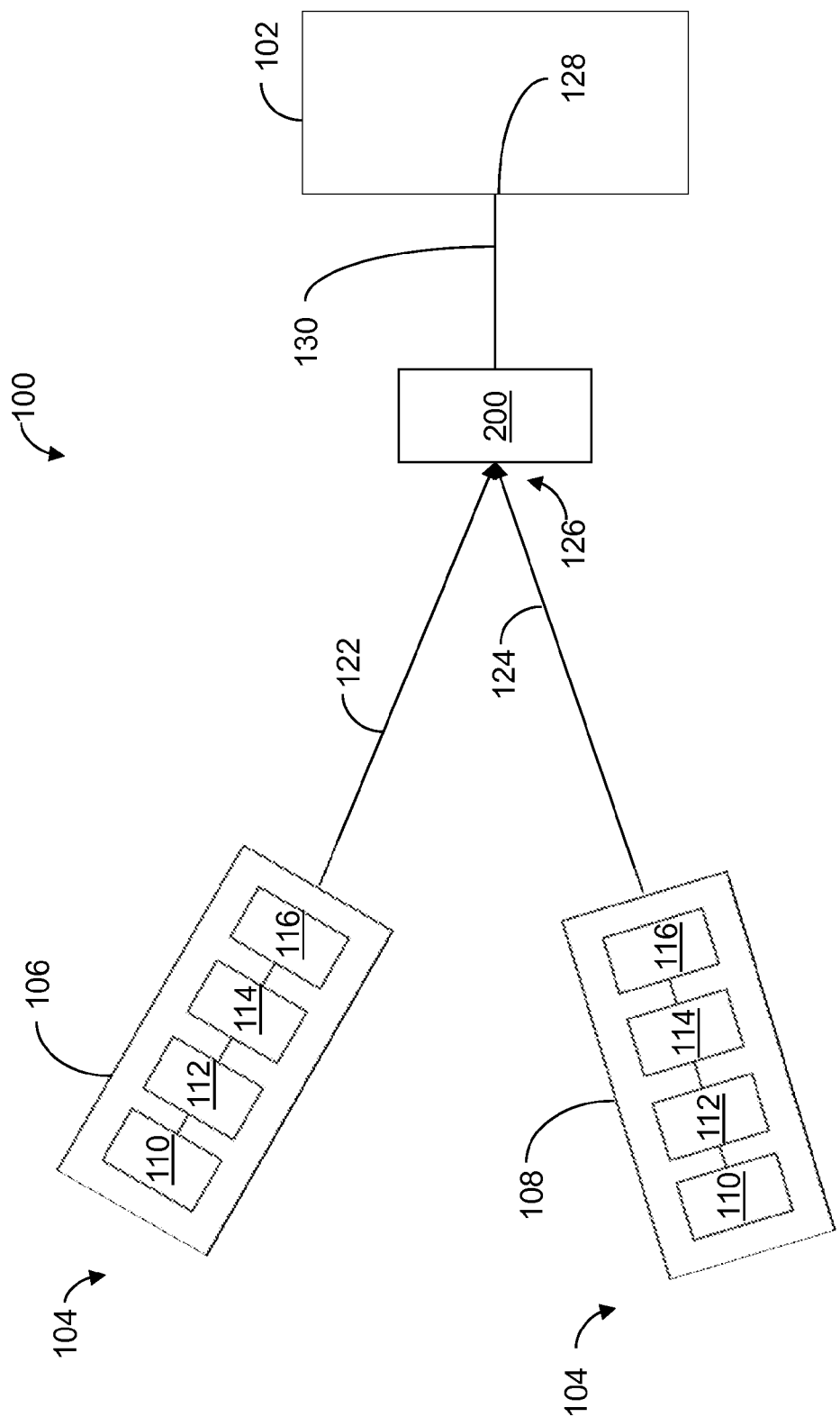
FIG. 2 illustrates an exemplary directed energy system including a non-linear mixing device that is used to mix the light beams before a beam is applied to the object.

FIG. 2 illustrates an exemplary directed energy system 100 including a non-linear mixing device 200 that is used to mix light beams 122 and 124 to generate a third light beam 130 that is emitted towards object 102. Unless otherwise specified, similar components are identified in FIG. 2 with the same reference numerals used in FIG. 1.

In the exemplary embodiment, directed energy system 100 includes transmitters 106 and 108 and non-linear mixing device 200. Non-linear mixing device 200 is between object 102 and first and second transmitters 106 and 108 to enable mixing device 200 to receive first and second light beams 122 and 124 and to enable third light beam 130 to be emitted towards object 102. Non-linear mixing device 200 may be manufactured from known non-linear optical crystals, which include, but are not limited to only including, β-barium borate, lithium iodate, potassium niobate, monopotassium phosphate, lithium triborate, potassium titanyl phosphate, lithium niobate, and ammonium dihydrogen phosphate.

In the exemplary embodiment, the interaction of beams 122 and 124 causes a third light beam 130 to be generated with a harmonic frequency that is different than that of beams 122 and 124 (i.e., a frequency that is approximately two times the frequency of beams 122 and 124), and/or third light beam 130 has a second order combination (i.e., a second order effect) as compared to beams 122 and 124. The second order effect may cause third light beam 130 to have a frequency that is approximately equal to a sum of the frequencies of beams 122 and 124, and/or a frequency that is approximately equal to a difference between the frequencies of beams 122 and 124. Alternatively or additionally, the frequency of third light beam 130 may be at any other combination of the frequencies of beams 122 and 124.

Non-linear mixing device 200 guides and emits third light beam 130 towards object surface 128 such that beam 130 interacts with surface 128 in a non-linear fashion to create material excitations across a part of surface 128. The interaction on surface 128 creates an effective energy transfer that facilitates a change in the physical state of object 102. More specifically, an efficiency of system 100 is facilitated to be enhanced and increased as compared to at least some known directed energy systems.

Figure 3:
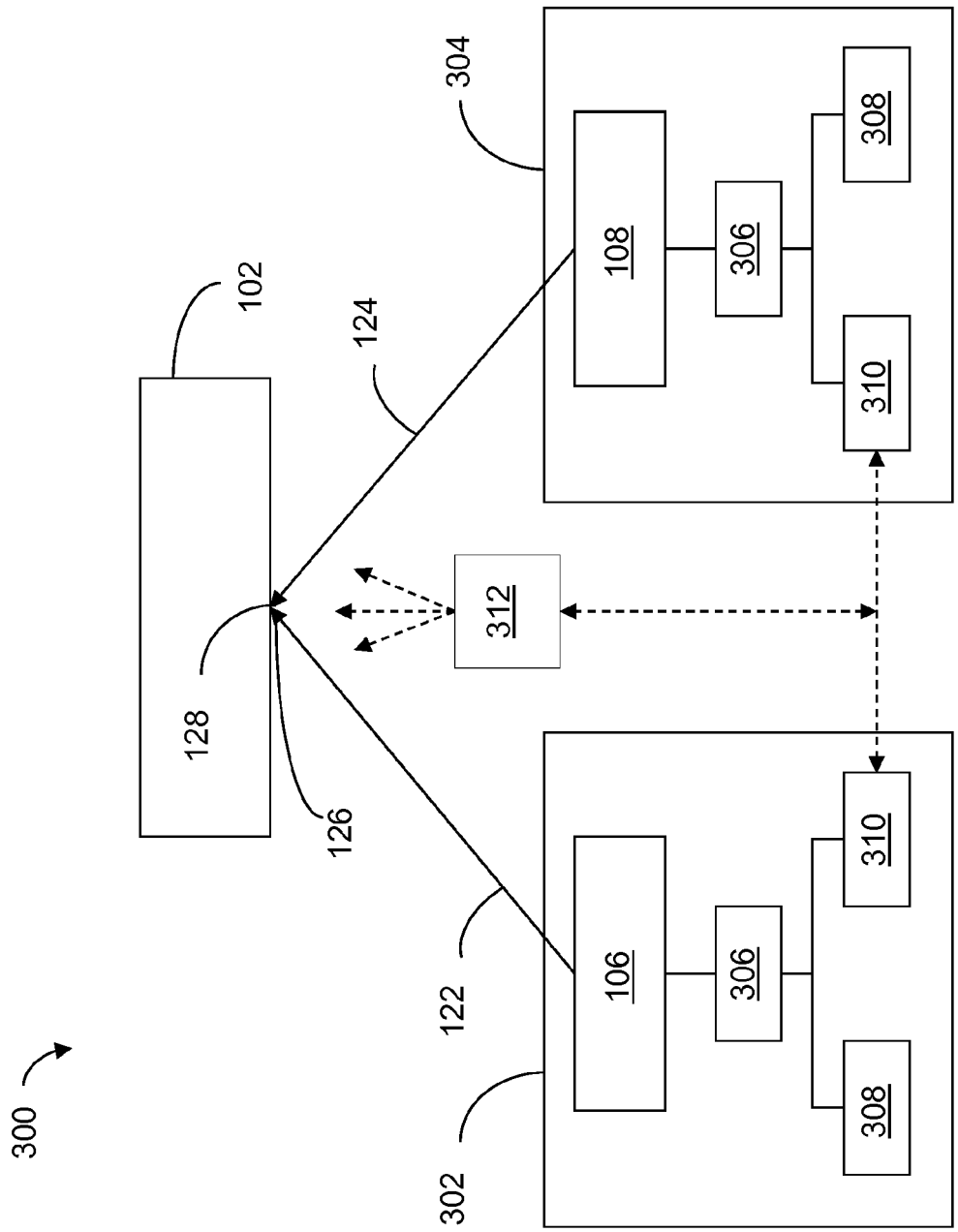
FIG. 3 illustrates an alternative directed energy system that may be used to apply directed energy on an object and/or that may be used to change a physical characteristic of the object.

FIG. 3 illustrates an alternative directed energy system 300 that may be used to apply directed energy on an object 102 and/or that may be used to change a physical characteristic of object 102. Directed energy system 300 is similar to directed energy system 100 (shown in FIG. 1), and similar components are identified in FIG. 3 with the same reference numerals used in FIG. 1.

In the exemplary embodiment, directed energy system 300 includes a first transmitter system 302 and a second transmitter system 304. First transmitter system 302 includes first transmitter 106, and second transmitter system 304 includes second transmitter 108. Moreover, first transmitter system 302 and second transmitter system 304 each includes a processor 306, a memory 308, and a communication device 310 for use in communicating with each other.

Processor 306 includes any suitable programmable circuit including one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor."

Memory 308 includes a computer readable storage medium, such as, without limitation, random access memory (RAM), flash memory, a hard disk drive, a solid state drive, a diskette, a flash drive, a compact disc, a digital video disc, and/or any suitable memory. In the exemplary embodiment, memory 308 includes data and/or instructions that are executable by processor 306 to enable processor 306 to perform the functions described herein.

Communication device 310 may include, without limitation, a radio frequency (RF) transceiver, a network interface controller (NIC), a network adapter, and/or any other communication device that enables directed energy system 300 to operate as described herein. Communication devices 310 transmit data to, and receive from, with each other using any suitable communication protocol.

In the exemplary embodiment, data is transmitted between transmitter systems 302 and 304 to facilitate applying directed energy to object 102. For example, first transmitter system 302 may transmit, to second transmitter system 304, a frequency at which first transmitter system 302 emits first light beam 122. Additionally or alternatively, second transmitter system 304 may transmit, to first transmitter system 302, a frequency at which second transmitter system 304 emits second light beam 124. Processor 306 of first transmitter system 302 and/or of second transmitter system 304 may calculate the frequencies at which to emit beams 122 and 124 such that when mixed at focal point 126, beams 122 and 124 interact with object 102 at its resonant frequency.

In one embodiment, a frequency of light beam 122 is controlled or selected by processor 306 of first transmitter system 302 to reduce an interference with ambient air or an ambient environment. Moreover, processor 306 may communicate, via communication devices 310, position and/or aim of transmitter systems 302 and 304 with respect to object 102 to facilitate aligning beams 122 and 124. Additionally or alternatively, any other data may be transmitted between transmitter systems 302 and 304.

In an alternative embodiment, directed energy system 300 includes an object monitoring system 312 communicatively coupled to communication devices 310. Object monitoring system 312 monitors and/or senses various characteristics relating to object 102 and communicates them to directed energy system 300. For example, object monitoring system 312 may monitor whether beams 122 and 124 are interacting at focal point 126. If interaction is not occurring, object monitoring system 312 communicates with communication devices 310 to adjust the aim of transmitter system 302 and/or 304. Object monitoring system 312 may also monitor physical characteristics of object 102 to determine and communicate a status of a variety of operating parameters, including but not limited to, health and/or physical state of object 102, whether and/or to what extent beams 122 and 124 at their designated frequencies are altering physical characteristics of object 102, and whether any foreign objects such as humans or vehicles enter a predetermined radius of danger with respect to object 102.

During operation, in the exemplary embodiment, a particular object 102 to be altered is selected and at least one resonant frequency is determined for object 102. In one embodiment, resonant frequency information for specific objects 102 is stored in a database or library that can be accessed by a user. In another embodiment, directed energy system 100 may use transmitters 106 and 108 to scan object 102 for its resonant frequency. More specifically, first transmitter 106 emits first light beam 122 at a substantially constant first frequency, while second transmitter 108 scans a range of frequencies using second light beam 124 until the resonant frequency of object 102 is determined.

In the exemplary embodiment, first transmitter system 302 uses first transmitter 106 to emit a first light beam 122 towards focal point 126, which may be a point on surface 128 of object 102 or a point on non-linear mixing device 200. Second transmitter system 304 emits a second light beam 124 towards focal point 126. Beams 122 and 124 interact to generate third light beam 130 with a third frequency that is different that the frequencies of beams 122 and 124. Third beam 130 interacts with a resonant frequency of object 102 to generate material excitations on surface 128 and to facilitate a more expedient change in the physical state of object 102.

Figure 4:
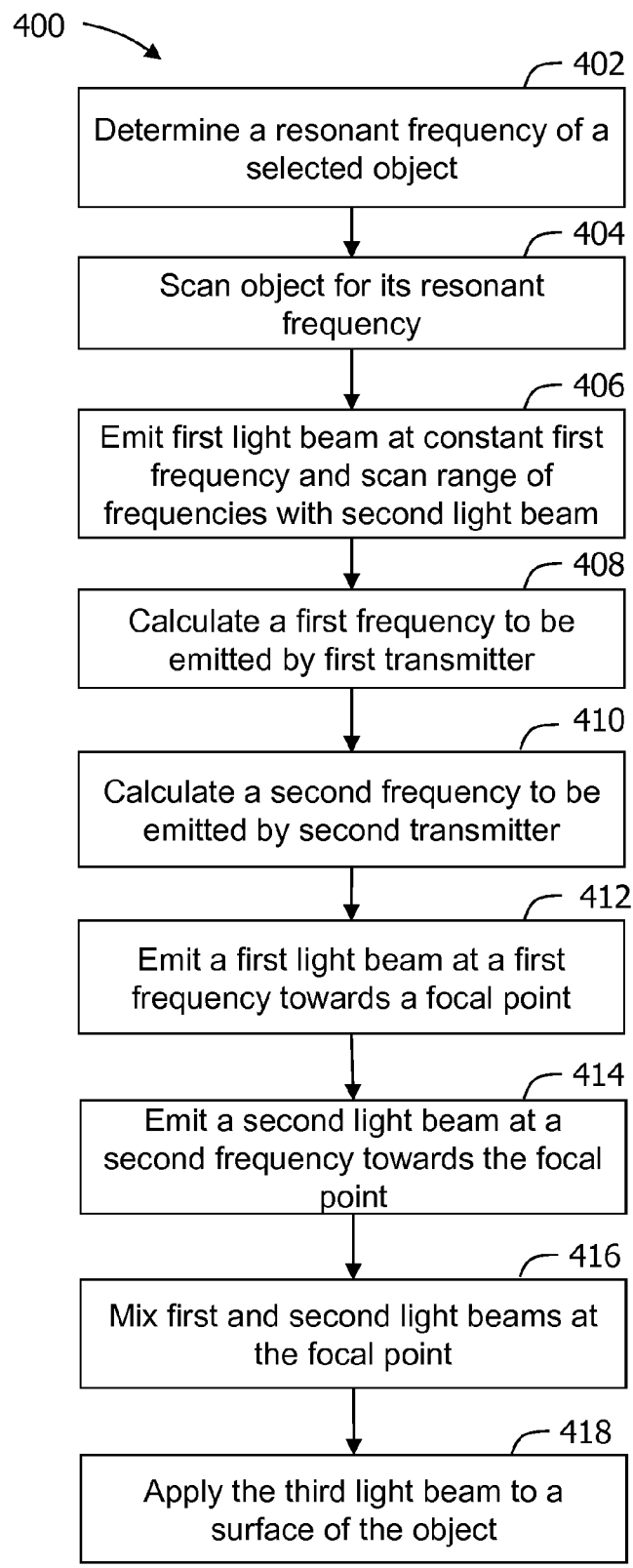
FIG. 4 is a flow diagram of an exemplary method that may be executed to apply directed energy to an object.

FIG. 4 is a flow diagram of an exemplary method 400 that may be used to direct energy to object 102 and that may be used with directed energy system 100 (shown in FIG. 1) and/or 300 (shown in FIG. 3). In the exemplary embodiment, method 400 is at least partially executed by a processor, such as processor 306 (shown in FIG. 3).

In the exemplary embodiment, method 400 includes determining 402 at least one resonant frequency of a selected object 102 (shown in FIGS. 1, 2, and 3). In one embodiment, resonant frequency information for specific objects 102 is stored in a database or library. In another embodiment, directed energy system 100 scans 404 object 102 to determine its resonant frequency. More specifically, in such an embodiment, first light beam 122 is emitted 406 at a substantially constant first frequency, while scanning a range of frequencies using second light beam 124.

In the exemplary embodiment, a processor 306 calculates 408 a first frequency to be emitted by first transmitter 106 and calculates 410 a second frequency to be emitted by second transmitter 108, based on the resonant frequency returned for object 102.

First light beam 122 having a first frequency is emitted 412 towards a predetermined focal point 126. Second light beam 124 is emitted 414 at a second frequency towards focal point 126. In one embodiment, beams 122 and 124 are focused on surface 128. In another embodiment, beams 122 and 124 are focused towards non-linear mixing device 200.

Beams 122 and 124 are mixed 416 at focal point 126 to generate a third light beam 130 having a third frequency that is coincident with at least one resonant frequency of object 102. In one embodiment, mixing beams 122 and 124 causes a third frequency to be generated that is a non-linear combination of the first frequency and the second frequency. In another embodiment, beams 122 and 124 are mixed to interact non-linearly with each other and with surface 128 to generate a third frequency that is a second order combination of the first and second frequencies. In such an embodiment, the third frequency may be one of a sum of the first and second frequencies and a harmonic of the first and second frequencies. In the exemplary embodiment, the third light beam 130 is then applied 418 to surface 128 to facilitate applying directed energy at object 102 and/or changing a physical characteristic of object 102.

The directed energy system described herein enables directed energy to be applied to an object and/or enables a physical characteristic of an object to be changed in a robust and efficient manner. The directed energy system emits a first light beam at a first frequency and a second light beam at a second frequency towards a focal point, wherein the beams are mixed non-linearly with a surface of the object. The interaction of the surface and the light beams creates material excitations on the object that creates an alteration and/or destruction of the object. The frequencies of the first and second light beams may be selected to be coincident with resonances in the object, so energy transfer may occur more effectively, and such that a rapid change in the physical characteristic of the object may occur. In addition, the frequencies of the first and second light beams may be selected to facilitate reducing environmental scattering and/or absorption, in conjunction with the non-linear response of the surface to the light beams. As such, an efficiency of the directed energy system may be increased as compared to at least some prior art systems.

Exemplary embodiments of directed energy systems and methods for applying directed energy to an object are described above in detail. The directed energy systems and the methods are not limited to the specific embodiments described herein but, rather, components of the systems and/or steps of the methods may be utilized independently and separately from other components and/or steps described herein. Further, the described operations and/or components may also be defined in, or used in combination with, other systems, methods, and/or devices, and are not limited to practice with only the directed energy system as described herein.

Although the present embodiments are described in connection with applying directed energy to an object, the embodiments are operational to detect or determine other aspects or characteristics of objects. The directed energy systems described herein are not intended to suggest any limitation as to the scope of use or functionality of any aspect of the disclosure. In addition, the directed energy systems described herein should not be interpreted as having any dependency or requirement relating to any one or combination of components illustrated in the exemplary operating environment.

The order of execution or performance of the operations in the embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for applying directed energy to an object, said system comprising:
    a first transmitter comprising a light source configured to emit a first light beam at a first frequency towards a focal point; and
    a second transmitter comprising a light source configured to emit a second light beam at a second frequency towards the focal point, the second transmitter configured to scan a range of frequencies using the second light beam, the second light beam emitted to cause a third light beam to be generated that has a third frequency that is coincident with at least one resonant frequency of the object, wherein at least one of the first transmitter and the second transmitter is configured to determine the at least one resonant frequency of the object.

2. A system in accordance with claim 1, wherein said first and second transmitters emit towards the focal point located on a surface of the object.

3. A system in accordance with claim 1, wherein said first and second transmitters emit towards the focal point located on a non-linear mixing device.

4. A system in accordance with claim 1, wherein the first light beam and the second light beam interact non-linearly with each other and with a surface of the object to generate the third frequency.

5. A system in accordance with claim 4, wherein the non-linear combination of the first frequency and the second frequency is a second order combination of the first frequency and the second frequency.

6. A system in accordance with claim 5, wherein the second order combination of the first frequency and the second frequency is a sum of the first frequency and the second frequency.

7. A system in accordance with claim 5, wherein the second order combination of the first frequency and the second frequency is a harmonic of the first frequency and the second frequency.

8. A system in accordance with claim 1, wherein the first and second transmitters are configured to determine the resonant frequency of the object.

9. A system in accordance with claim 8, wherein at least one of the first transmitter and the second transmitter is configured to calculate the first and second frequencies to be emitted based on the determined resonant frequency.

10. A system in accordance with claim 8, wherein the first transmitter is configured to emit the first light beam at a substantially constant first frequency.

11. A method of applying directed energy to an object, said method comprising:
    emitting a first light beam at a first frequency towards a focal point;
    emitting a second light beam at a second frequency towards the focal point;
    determining the resonant frequency of the object by scanning a range of frequencies using the second light beam;
    mixing the first and second light beams to cause a third light beam to be generated that has a third frequency that is coincident with at least one resonant frequency of the object; and
    applying the third light beam to a surface of the object.

12. A method in accordance with claim 11, further comprising emitting the first and second light beams towards the focal point located on a surface of the object.

13. A method in accordance with claim 11, further comprising emitting the first and second light beams towards the focal point located on a non-linear mixing device.

14. A method in accordance with claim 11, further comprising causing the first light beam and the second light beam to interact non-linearly with each other and with the surface to generate the third frequency.

15. A method in accordance with claim 14, further comprising causing the first light beam and the second light beam to interact non-linearly with each other and with the surface to generate the third frequency that is a second order combination of the first frequency and the second frequency.

16. A method in accordance with claim 15, wherein generating the third frequency comprises generating the third frequency that is a sum of the first frequency and the second frequency.

17. A method in accordance with claim 15, wherein generating the third frequency comprises generating the third frequency that is a harmonic of the first frequency and the second frequency.

18. A method in accordance with claim 11, further comprising calculating the first and second frequencies to be emitted based on the determined resonant frequency.

19. A method in accordance with claim 11,
    further comprising determining the resonant frequency of the object by emitting the first light beam at a substantially constant first frequency.

* * * * *